United States Patent [19]

Kelman

[11] 4,398,812
[45] Aug. 16, 1983

[54] APPARATUS AND METHOD FOR MEASURING THE ANTERIOR CHAMBER DIAMETER OF THE EYE

[76] Inventor: Charles D. Kelman, 73 Bacon Rd., Old Westbury, N.Y. 11568

[21] Appl. No.: 160,911

[22] Filed: Jun. 18, 1980

[51] Int. Cl.³ .............................................. A61B 3/10
[52] U.S. Cl. .................................. 351/205; 351/211; 351/213; 351/214
[58] Field of Search ....................... 351/6, 13, 16, 205, 351/211, 213, 214, 221; 350/10, 30; 356/372, 383, 384, 392, 393, 394, 397; 33/125 A, 174 D, 178 R, 178 B

[56] References Cited

U.S. PATENT DOCUMENTS

| | | | |
|---|---|---|---|
| 2,016,780 | 10/1935 | Hartinger | 351/13 |
| 2,430,851 | 11/1947 | Allen | 351/6 |
| 3,174,392 | 3/1965 | Rantsch | 33/125 A |
| 3,589,800 | 6/1971 | Cardona | 351/16 |
| 3,765,764 | 10/1973 | Niss | 356/372 |
| 3,804,528 | 4/1974 | Kilmer et al. | 356/392 |
| 4,007,980 | 2/1977 | Bracher et al. | 351/6 |
| 4,309,085 | 1/1982 | Morrison | 351/6 |
| 4,319,564 | 3/1982 | Karickhoff | 33/174 D |

*Primary Examiner*—R. A. Rosenberger
*Attorney, Agent, or Firm*—Henry Sternberg

[57] ABSTRACT

An apparatus and method for measuring the anterior chamber diameter of the eye is disclosed in which a device illuminates the opposite end points of the annular groove. A gauging device cooperates with the illuminating device so as to provide to the viewer through a goneal assembly, a recognizable signal corresponding to a measure of the distance between the end points for gauging the distance.

14 Claims, 8 Drawing Figures

APPARATUS AND METHOD FOR MEASURING THE ANTERIOR CHAMBER DIAMETER OF THE EYE

The present invention relates to a new apparatus and method for measuring the anterior chamber diameter of the eye.

The anterior chamber of the human eye is a hemispherically-shaped aqueous-containing space bounded anteriorly by the cornea and posteriorly by the iris. Artificial lenses which are designed for implantation within the anterior chamber are referred to as anterior chamber intraocular lenses.

The recent increase in intraocular lens implantations in the United States has accelerated the development of anterior chamber intraocular lenses. Recently, several implant lenses and methods of implantation have been introduced. A new intraocular lens construction and a method of implantation is described in my U.S. Pat. No. 4,092,743.

Many anterior chamber intraocular lens currently in use consist of a lens member and a support structure. The support structure functions to secure the lens member within the anterior chamber. Examples of this type of implant lens are disclosed in my aforementioned U.S. Pat. No. 4,092,743.

Accurate measurement of the anterior chamber diameter is necessary to achieve a proper fit of the intraocular lens in the anterior chamber, and to avoid both incorrect insertion and damage to the chamber structure. The anterior chamber diameter is the length of an imaginary straight line joining two diametrically opposite end points of the annular groove which is formed by the posterior surface of the cornea and anterior surface of the iris.

Several devices are known for measuring the anterior chamber diameter during surgery. I previously developed an elongated, slender, graduated, probe-type of instrument commonly known as the "Kelman Dipstick" for measuring the anterior chamber diameter. After the surgical incision is made preparatory to implantation of an intraocular lens, the dipstick is passed through the incision into the anterior chamber while being viewed by the practitioner through the cornea with the aid of an optical device. The dipstick is calibrated so that the distance from the pupillary axis to the annular groove may be determined by viewing the dipstick. This distance is then doubled to establish the size of the lens required for implantation. The dipstick technique of measurement is often time consuming and undesirably lengthens the surgical procedure. In addition, a possible complication of the dipstick technique may be a hyphema secondary to trauma to the trabecular meshwork circumferentially surrounding the annular groove resulting from contact with the tip of the dipstick. Significantly, the graduated dipstick technique of measurement does not allow the practitioner to determine the proper anterior chamber intraocular lens size until after an incision is made in the patient's eye. As a result, the practitioner must undesirably keep on hand, during the operation, a large inventory of intraocular lenses of different sizes.

Until the present invention, an accurate determination of the anterior chamber diameter could be made only during a surgical procedure, such as in a manner just described. I have now, however, discovered a method for accurately determing the anterior chamber diameter without requiring surgery. I have determined that by moving a projected beam of light along an imaginary line containing the diameter of the anterior chamber, from a position, along such diameter, outwardly of the annular groove, toward the optic axis, there was a distinct location during such movement where an end point of the diameter of the annular groove was illuminated by the beam. This location is just inwardly, i.e. closer to the optic axis, of the light-impervious ciliary body. Movement of the projected light beam back out of the location in a direction outwardly, i.e. away from the optic axis, results in a distinct loss of illumination resulting in the region becoming dark once more as if the light had been turned off. It is this instantaneous change from darkness to light, as viewed through an optical device, which permits an accurate determination of the location of both of the diametrically opposite end points of the annular groove. Thus, the anterior chamber diameter can be determined from the positions of the light beams at the time of illumination of the end points.

The light-impervious nature of the ciliary body is also utilized in a determination of the anterior chamber diameter with the use of colored lines of light. A series of parallel lines of light are projected through the transparent corneal surface of the eye onto a plane substantially perpendicular to the optic axis containing the annular groove at opposite sides of the optic axis. Each line of light within a series is a different color than and adjacent to other lines of light within the same series. The colored lines of light are spaced apart from one another at predetermined distances. By establishing through an optical device the color of the line of light just inwardly, i.e. closer to the optic axis, of the ciliary body which illuminates each end point the distance between the end points, or anterior chamber diameter, is determinable as it corresponds to the predetermined distance between the colored lines. Concentric arcs of light can also be used to determine the anterior chamber diameter where each arc has a different color and the optic axis passes through the common origin. The arcs of colored light are formed into two series and focused onto the plane of the annular groove, with one series at an opposite side of the optic axis from the other series, so that an arc of colored light from each series illuminates an end point of the annular groove. The distances between the arcs of both series are predetermined so that the distance between the end points can be established when determining the color of the arc illuminating each end point. The anterior chamber diameter correspond to the predetermined distance between the arcs of colored lights responsible for illuminating the end points.

Accordingly, it is an object of this invention to provide an ocular device for accurately measuring anterior chamber diameter which overcomes the shortcomings, problems and disadvantages of the prior art anterior chamber diameter-measuring devices previously described.

It is another object of this invention to provide an ocular device by which measurement of the anterior chamber diameter may be performed during a pre-surgery office examination of the anterior chamber so as to enable practitioners to determine proper anterior chamber introcular lens size before surgery, and thereby virtually eliminate the need for the practitioner to maintain a large inventory of anterior chamber intraocular lenses in different sizes.

It is yet another object of this invention to provide an ocular device by which rapid and accurate measurement of anterior chamber diameter may be performed prior to surgery so as to substantially reduce the time heretofore required for intraocular lens implantation surgery, when the chamber diameter had to be measured during the surgery.

It is still another object of this invention to provide a simple and accurate method, without requiring surgical procedure, for measuring the anterior chamber diameter.

Basically, the objectives of the present invention are achieved by utilizing a device for illuminating the opposite end points of the annular groove. A gauging device cooperates with the illuminating device so as to provide to the viewer, through a viewing device, a recognizable signal corresponding to a measure of the distance between the end points for gauging the distance. For example, two light sources are utilized, each of which are positionally adjustable and operable for projecting a line of light toward the surface of the eye. The lines of light are projected parallel to one another and on opposite sides of the optic axis so as to perpendicularly intersect an imaginary straight line containing a diameter of the anterior chamber. The light sources are moved so as to move the projected lines of light along this imaginary line from positions outwardly of the diametrically opposite end points of the annular groove toward the rspective end points. The lines of light are moved along this imaginary line until the respective end points are initially illuminated by the lines of light tangentially impinging the annular groove, as viewed through a viewing device which is positioned proximate to the corneal surface. The opposite end points of the annular groove are defined by the intersection between the imaginary line and the peripheral interior surface of the annular groove. A measuring device is used to determine the distance between the opposite end points as a function of the position of the light sources when the latter have illuminated the end points. This distance corresponds to the length of the anterior chamber diameter.

The distance can also be determined by forming two series of colored lines of light on the plane of the annular groove with one series at an opposite side of the optic axis from the other series. Each line of light is adjacent to and a different color than the other lines of light in the same series. The colored lines of light are parallel to each other with the perpendicular distance between the lines of both series being predetermined. By proper positioning each end point is illuminated by a colored line of light from a series. Upon a determination of the color of the line of light responsible for the illumination of each end point, the distance between the end points, or the anterior chamber diameter, can be determined as it corresponds to the predetermined distance between the colored lines of light illuminating the end points. The end points can similarly be illuminated with two series of concentric arcs of light projected onto the plane of the annular groove with one series at an opposite side of the optic axis from the other series. Each arc of light in a series has a different color than the other arcs in the same series and all arcs have the optic axis as the origin. The distance between the colored arcs of light of one series and the colored arcs of the other series are predetermined. By proper positioning each end point is illuminated by a colored arc of light from a series. The distance between the end points is then determined from the color of the arc of light illuminating each end point. The anterior chamber diameter corresponds to the predetermined distance between the arcs of colored lights responsible for illuminating the end points.

The foregoing and other objects, characteristics and advantages of the present invention will be more clearly understood from the following detailed description thereof when read in conjunction with the accompanying drawings, in which.

Figure 1:
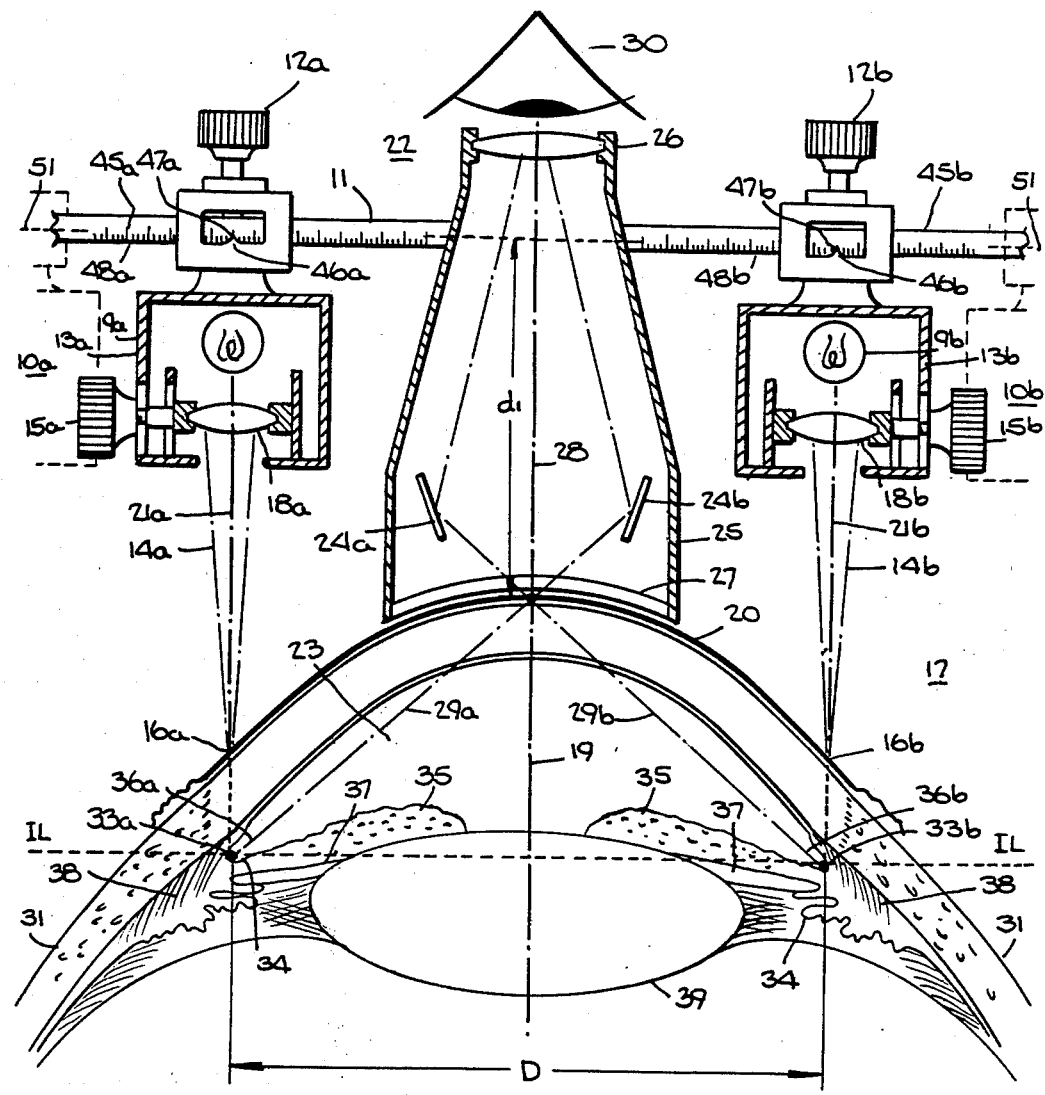
FIG. 1 is a plan view of an optical device in accordance with the present invention together with a schematic sectional view of an eye to be measured.

Referring now to the drawings wherein the same reference numerals have been used throughout to designate like elements, and wherein the letters a and b have been appended to indicate left and right components, respectively. An ocular device according to one embodiment of the present invention is shown in FIG. 1 in which a pair of light sources 10a, 10b are mounted on a longitudinal support member 11 so as to be laterally movable towards and away from one another and capable of being locked by use of knobs 12a, 12b along the longitudinal member 11 in different positions. Light bulbs 9a, 9b are located within housings 13a, 13b from which they project beams of light 14a, 14b that are capable of being focused by focusing knobs 15a, 15b to form lines of light 16a, 16b on the surface of the eye 17 that are parallel to each other. The knobs 15a, 15b focus the light beams 14a, 14b by adjusting the distance between lenses 18a, 18b and light bulbs 9a, 9b. The longitudinal support member 11 is positioned substantially perpendicular to and preferably intersects with the optic axis 19 of the eye 17, with each of the light sources 10a, 10b being positioned on opposite sides of the optic axis 19. The light sources 10a, 10b are operable to project the beams of light 14a, 14b onto the corneal surface 20 of the eye 17, with the beams 14a, 14b having their longitudinal axes 21a, 21b, parallel to the optic axis 19.

A goneal device 22 is used for examination of the anterior chamber 22 of the eye 17. The goneal device 22 is composed of at least two goneal mirrors 24a, 24b, a housing 25, an eyepiece 26, and a lens 27. The lens 27 is positioned near to, or on the corneal surface 20 of the eye 17 in a manner so that longitudinal axis 28 of the device 22 and optic axis 19 are coaxial. The mirrors 24a, 24b are positioned within the goneal housing 25 so as to reflect through the eyepiece 26, light rays 29a, 29b passed through the lens 27. The goneal device 22 is affixed to the longitudinal member 11 in a manner so that the goneal device 22 and a viewer 30 do not interfere with the projection of the light beams 14a, 14b onto the corneo-sceleral surface 20, 31 of the eye 17. The invention is also operable if the goneal device 22 is supported by other than the longitudinal support member 11, for example, by a separate and independent frame (not shown). The goneal device 22 is positionable so that the viewer 30 can observe through the eyepiece 26 diametrically opposite end points 33a, 33b of the annular groove 34 within the anterior chamber 23 when the end points 33a, 33b are illuminated by the light beams 14a, 14b. The annular groove 34 is located within the anterior chamber 23 and is formed by the posterior surface of the cornea 20 and the anterior surface of the iris 35. Posterior to the iris is the lens 39 of the eye 17. At the junction of the cornea 20 and the iris 35 an anterior chamber angle 36 is formed. Posterior to and outwardly from the annular groove 34 and circumferentically surrounding the posterior chamber 37 is the light-impervious ciliary body 38. It is the light-impervious characteristic of the ciliary body that facilitates detection through the goneal device 22 of the end points 33a, 33b of the annular groove 34. This is due to the instantaneous and distinct change from darkness to light which occurs, as viewed through the goneal device 22, when the lines of light 16a, 16b are moved toward the optic axis 19 from positions respectively outwardly of the ciliary body 38 i.e. further spaced from the optic axis 19, to positions respectively just inwardly of the ciliary body 38, so as to tangentially impinge the annular groove 34 at the end points 33a, 33b thereby illuminating the latter.

The light sources 10a, 10b are initially positioned along the longitudinal support member 11 so as to project the light beams 14a, 14b towards points in space along an imaginary line IL and onto the scleral surface 31 on opposite sides of the optic axis 19. The imaginary line IL contains an anterior chamber diameter having end points 33a, 33b, defined by the points of intersection of the imaginary line IL with the peripheral surface of the annular groove 34. These end points 33a, 33b also correspond to vertices of the anterior chamber angle 36. The longitudinal axis 51 of the longitudinal member 11 is positioned substantially parallel to the imaginary line IL. Each of the light sources 10a, 10b are then independently and progressively moved along the longitudinal support member 11 towards the optic axis 19 thereby moving the points in space along the imaginary line IL from locations along IL outwardly of the end points 33a, 33b, toward said end points respectively. Preferably, one of the light sources, for example 10a, is moved along the longitudinal support member 11 until it is properly positioned so that line of light 16a tangentially impinges the annular groove 34 at the end point 33a thereby illuminating the latter prior to movement of the second light source 10b along the longitudinal member 11. During this movement of the light sources 10a, 10b the light beams 14a, 14b are projected so that the two lines 16a, 16b impinge on the corneo-scleral surface 20, 31 of the eye 17 along at least part of a path or meridian passing through the optic axis 19.

Figure 2:
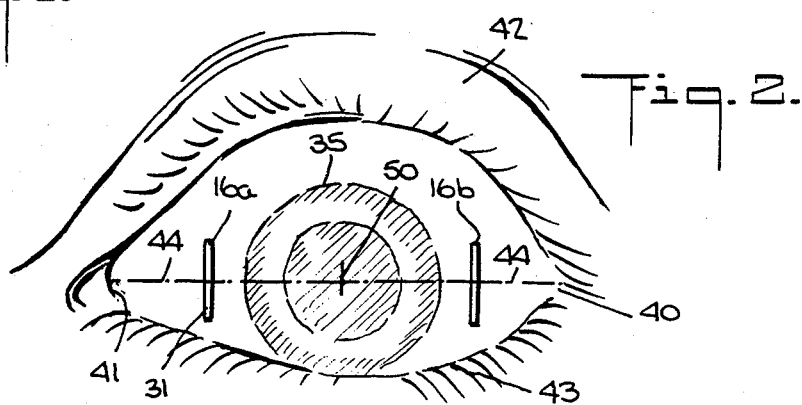
FIG. 2 is a schematic front elevational view of an eye showing external portions.

The eye 17, as shown in FIG. 2, has a medial canthus 40 and a lateral canthus 41 which correspond approximately to corner regions where the upper eyelid 42 and the lower eyelid 43 converge. The medial canthus 40 is the corner region closest to the nose and the lateral canthus 41 is the corner furthest from the nose. When the eye 17 is properly positioned and the longitudinal support member 11 is positioned parallel to the axis joining the medial canthus 40 and lateral canthus 41 then a path or portion of a meridian 44 on the surface of the eye is illuminated by lines of light 16a, 16b projected from sources 10a, 10b as they are moved along longitudinal support member 11. This path is defined by the medial canthus 40, a point 50 at the intersection of the corneal surface 20 and the optic axis 19, and the lateral canthus 41.

During movement of the light sources 10a, 103b along the longitudinal member 11, the anterior chamber 23 is observed by a viewer 30 through the eyepiece 26 of the goneal device 22 with the purpose of detecting the rays 29a, 29b reflected from the diametrically opposite end points 33a, 33b.

By moving the light sources 10a, 10b towards each other along the longitudinal member 11, from the dotted line position in FIG. 1 to the full line position in FIG. 1, the points in space are moved along the imaginary line IL, while the lines of light 16a, 16b are moved across the corneo-scleral surface 20, 31 of the eye 17 towards the optic axis 19. When either or both of the lines of light 16a, 16b projected by light beams 14a, 14b impinge on the ciliary body 38 the anterior chamber 23 appears dark to the viewer 30 observing the anterior chamber 23 through the eyepiece 26. However, as soon as one of the light sources, for example, light source 10a, is moved closer to the optic axis so as to project line of light 16a inwardly of the light-impervious ciliary body 38, the end point 33a of the imaginary diameter of annular groove 34 is illuminated by the line of light 16a tangentially impinging the annular groove 34 at the end point 33a. The light ray 29a reflected from the end point 33a passes through the lens 27 and is further reflected by the goneal mirror 29a through the eyepiece 26 to the viewer 30. As soon as the light ray 29a is detected or observed by the viewer 30, i.e. when the formerly dark end point 33a of the annular groove 34 has become illuminated, the light source 10a is locked into place along the longitudinal member 11 by use of a knob 12a. This procedure is repeated for the other light source 10b until the diametrically opposite end point 33b is illuminated. Thus, as soon as the light ray 29b is detected or is observed through the eyepiece 26, the light source 10b is locked into place. In order to facilitate detection throgh the eyepiece 26 and in order to diminish the possibility of any confusion as to the source of the light ray 29b, the light source 10a is preferably turned off after it is locked into place and prior to moving the light source 10b along the longitudinal member 11.

The longitudinal member 11 has scales 45a, 45b along its surface in the region where the light sources 10a, 10b are mounted and moved. The light sources 10a, 10b are equipped with pointers 46a, 46b which have apexes 47a, 47b aligned with longitudinal axes 21a, 21b of the beams 14a, 14b. The pointers 46a, 46b point to markings 48a, 48b on the scale 45a, 45b. The scales 45a, 45b are calibrated so that the markings 48a, 48b indicate the distance between the longituindal axes 21a, 21b of the two light sources 10a, 10b. Since the light beams 14a, 14b in this embodiment are projected parallel to the optic axis 19, the distance between the light sources 10a, 10b, when they are properly positioned for illuminating the end points 33a, 33b, as indicated on the scales 45a, 45b, corresponds to the diameter of the annular groove 34 and consequently to the anterior chamber diameter "D".

In the embodiment shown in FIG. 1, prior to the examination of the eye 17, the patient's head is positioned such that the point of intersection 50 of the optic axis 19 and corneal surface 20 is located a predetermined distance $d_1$ from the longitudinal axis 51 of the longitudinal member 11. This can be done by providing the patient with a positionally adjustable chin support and a forehead rest (not shown) for securing the patient's head in a predetermined position. For this embodiment, however, since the beams of light 14a, 14b are projected parallel to the optic axis 19, this distance $d_1$ does not enter into the determination of the anterior chamber diameter "D".

In a modification (not shown) of the embodiment shown in FIG. 1 the light sources focus the respective light beams into respective points of light that are projected toward respective points in space and onto the surface of the eye. The light sources are positionally adjusted so as to move the points of light along an imaginary line containing the diameter. The light beams are moved from positions outwardly of the annular groove toward the respective end points until the points of light impinge on and illuminate the diametrically opposite end points as viewed through the goneal device.

In a further modification of the above embodiment, in place of an observer, a photoelectric device (not shown) is positioned proximate to the eyepiece for detecting the light rays reflected from the end points. The light sources are electrically controlled for movement along the longitudinal member until the photoelectric device detects the illumination of end points at which time the photoelectric device transmits a signal which causes the movements of the light sources to cease. The anterior chamber diameter "D" is then determined from the positions of the light sources.

Figure 3:
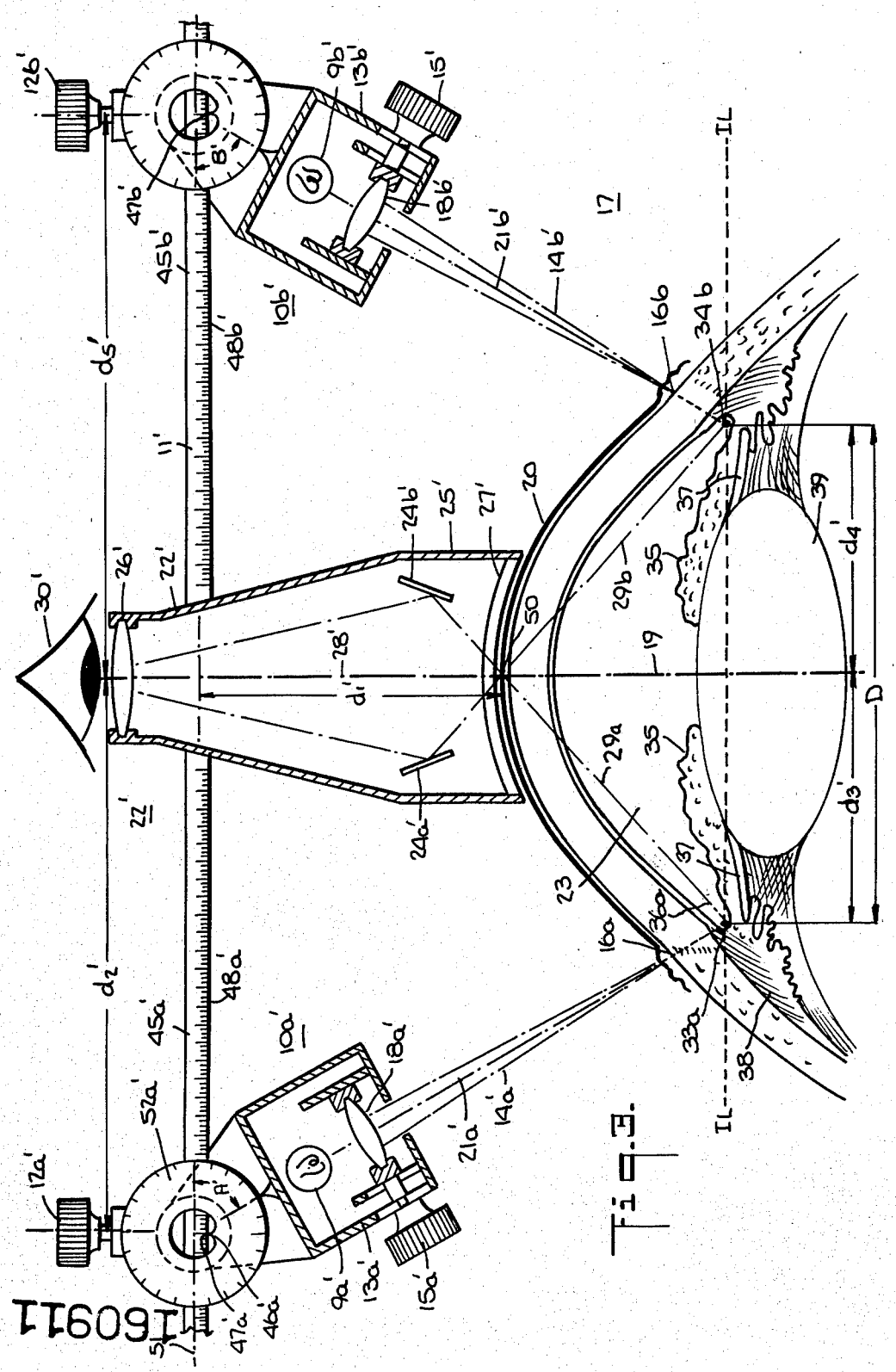
FIG. 3 is a plan view of an optical device according to another embodiment of the present invention.

FIG. 3 shows the ocular device arranged as in FIG. 1, with the additional feature that the light sources 10a', 10b' are pivotably mounted on the longitudinal member 11' so as to be operable to project light beams 14a', 14b' at adjustable converging angles A', B' with respect to the optic axis 19. By projecting the light beams 14a', 14b' at converging angles A', B' with respect to the optic axis 19 the light sources 10a', 10b' may be laterally located along the longitudinal member 11' further away from the optic axis 19 than in the embodiment shown in FIG. 1, wherein the light beams 14a, 14b are projected parallel to the optic axis 19.

The pivotable light sources 10a', 10b' are equipped with a device 52a', 52b' for measuring the angles A', B' formed between the longitudinal axes 21a', 21b' of the light beams 14a', 14b' and the longitudinal axis 51' of the longitudinal member 11 respectively.

In this embodiment shown in FIG. 3, in order to obtain an accurate measurement of the anterior chamber diameter "D" the distance from the point of intersection 50 of the optic axis 19 and the corneal surface 20 to the longitudinal axis 51' of the longitudinal member 11' is predetermined for each eye to be measured. This distance can be predetermined as previously mentioned, by the use of an adjustable chin support and forehead rest (not shown) but well known to the art.

The light sources 10a', 10b' are positioned on opposite sides of the optic axis 19 and the light beams 14a', 14b' are locked at predetermined positions along the longitudinal axis 51' of the longitudinal member 11' so that the light beams 14a', 14b' project lines of light 16a', 16b' towards points in space along imaginary line IL and onto the scleral surface 31 of the eye 17. The light sources 10a', 10b' are pivoted until the light beams illuminate end points 33a, 33b, at which time the light beams 14a', 14b' subtend determinable angles A', B' with respect to the longitudinal axis 51'. The illuminated end points 33a, 33b are observed or detected through the goneal device 22' as previously described. By establishing the perpendicular distance $d_1'$ from the point of intersection 50 of the optic axis 19 and corneal surface 20 to the longitudinal axis member 11', and the lateral distance $d_2'$ from the optic axis 19 to the light source 10a', together with the angle A' subtended between the longitudinal axis 21a' of light beam 14a' and the longitudinal axis 51' of the longitudinal support member 11', the distances $d_3'$ from the optic axis 19 to the end point 33a can be determined from the geometry of the trapezoid shown. This procedure is repeated for light source 10b' to obtain the measurement of the distance $d_4'$ which represents the distance between the end point 33b and the optic axis 19. It should be recognized in obtaining this distance measurement $d_4'$, that the lateral distance $d_5'$ from the light source 10b' to the optic axis 19 and the angle B' subtended by longitudinal axis 21b' of light beam 14b' and longitudinal axis 51' need not be the same as the corresponding distance $d_2'$ and angle A' established for light source 10a'. The distances $d_3'$ and $d_4'$ are added to arrive at the present measurement of the anterior chamber diameter "D".

Each of the converging angles A', B' is preferably in the range of between 60° and 90°.

In the embodiment shown in FIG. 3 the light sources 10a', 10b' are locked in predetermined locations along the longitudinal support member 11'. In addition, they are pivotably movable and capable of being locked in different angular positions with respect to the longitudinal support member 11'. It is apparent, however, that the anterior chamber diameter "D" can be determined if the light sources 10a', 10b' are both laterally positionable at adjustable distances from the optic axis 19 along the longitudinal axis 51' and are pivotable so as to project light beams 14a', 14b' at determinable converging angles A', B' when illuminating each of the end points 33a, 33b of the annular groove 34.

Figure 4:
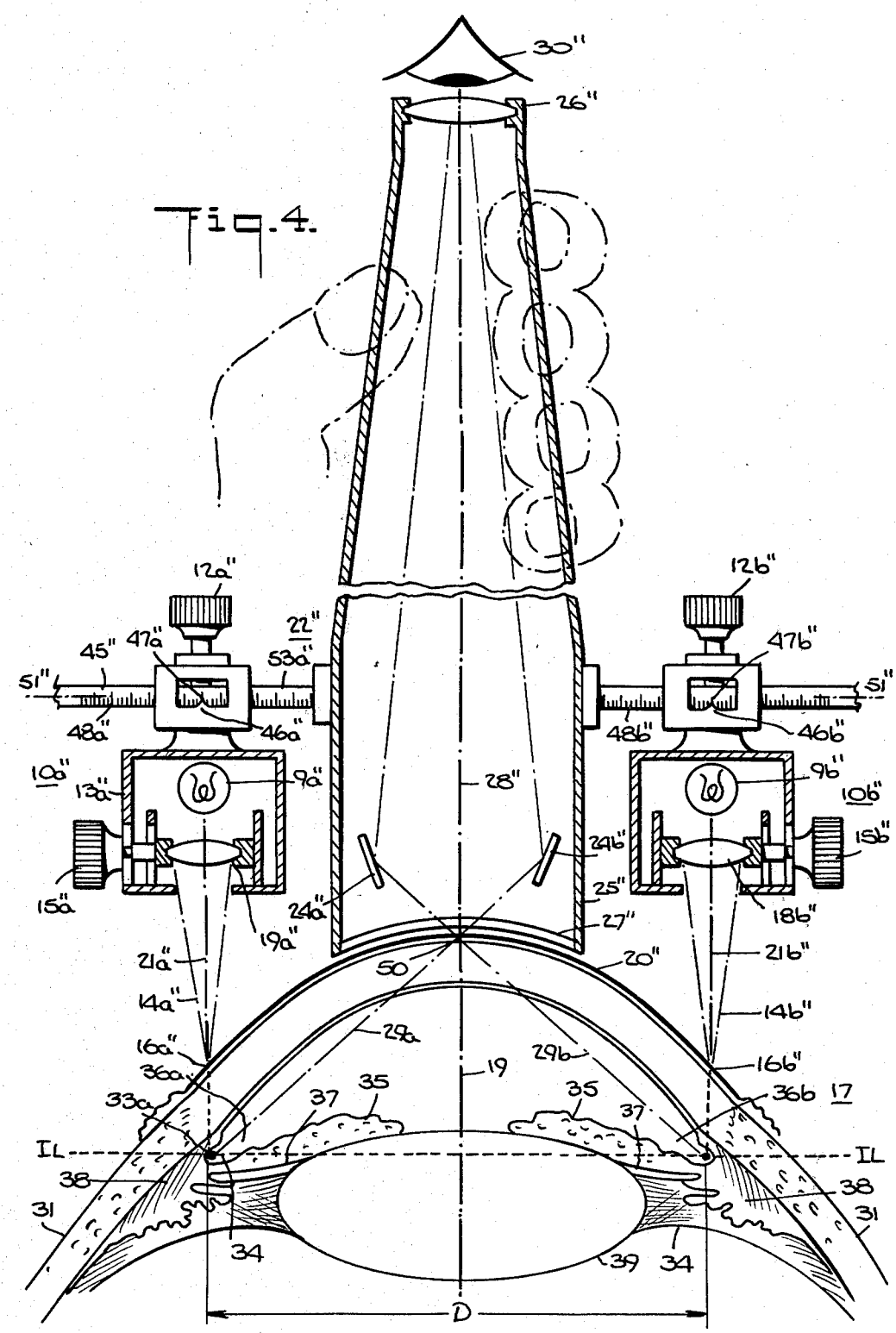
FIG. 4 is a plan view of an optical device according to an additional embodiment of the present invention.

Referring now to FIG. 4, goneal device 22" which is capable of being hand held is positioned centrally on the corneal surface 20" so that the longitudinal axis 28" of the housing 13" and the optic axis 19 of the eye 17 are coaxial. The goneal device 22" is positioned so as not to completely cover the corneal surface 20. Mounted on two opposite sides of the housing are colinear guide members 53a", 53b". These guide members 53a", 53b" may be located, as shown, near the lens 27" of the goneal device 22" or they may, be located closer to the eyepiece 26", without adversely affecting the measurement accuracy of the anterior chamber diameter "D". The light sources 10a", 10b" are mounted on the guide members 53a", 53b" so as to project light beams 14a", 14b" in the form of lines of light 16a", 16b" that are parallel to each other and parallel to the optic axis 19, and so as to be laterally movable along each of the guide member 53a", 53b" and positionally lockable thereupon by knobs 12a", 12b". The guide members 53a", 53b" extend from the housing 25" so as to be substantially parallel to the imaginary line IL and perpendicular to the optic axis 19 of the eye 17 when the goneal device 22" is placed in operable position over the corneal surface 20. The light sources 10a", 10b" are positioned so as to project light beams 14a", 14b" toward points in space along the imaginary line IL and onto the scleral surface 31 of the eye 17 on the opposite sides of the optic axis 19. The light sources 10a'', 10b'' are independently and progressively moved towards the optic axis 19 from positions outwardly of the first and second end points 33a, 33b of the annular groove 34. While moving along the guide members 53a'', the points in space are moved along the imaginary line IL and the light sources 10a'', 10b'' illuminate at least part of an optical path on the surface of the eye passing through the optic axis 19, with each light beam 14a'', 14b'' illuminating a portion of this path on its respective side of the optic axis 19. During the movement of the light sources 10a'', 10b'' the anterior chamber 23 is simultaneously viewed through the eyepiece 26'' of the goneal assembly 22''. Along the guide member 53a'', 53b'' are scales 45a'', 45b'' indicating the location of each of the light sources 10a'', 10b'' with respect to the optic axis 19. The lines of light 16a'', 16b are moved toward the optic axis 19 from positions respectively outwardly of the ciliary body 38 i.e. further spaced from the optic axis 19 to positions just inwardly of the ciliary body 38 so as to tangentially impinge the annular groove 34 at the end points 33a, 33b thereby illuminating the latter. From the position of the light sources 10a'', 10b'' at the time when the end points 33a, 33b are first illuminated, the anterior chamber diameter "D" can be determined, in the manner already described above.

In a modification (not shown) of this embodiment, the guide members are affixed relative to the housing at a predetermined distance from the point of intersection of the optic axis and the corneal surface so that light sources project beams of light at predetermined converging angles with respect to the optic axis. The anterior chamber diameter is then determined from the geometry of the trapezoids, as discussed previously.

Preferably the goneal housing 25'' and guide members 53a'', 53b'' are integral. However, it is also possible to have a separate unit consisting of guide members 53a'', 53b'' and light sources 10a'', 10b'' with scales 45a'', 45b'' that is attachable to an existing goneal assembly 22''.

Figure 5:
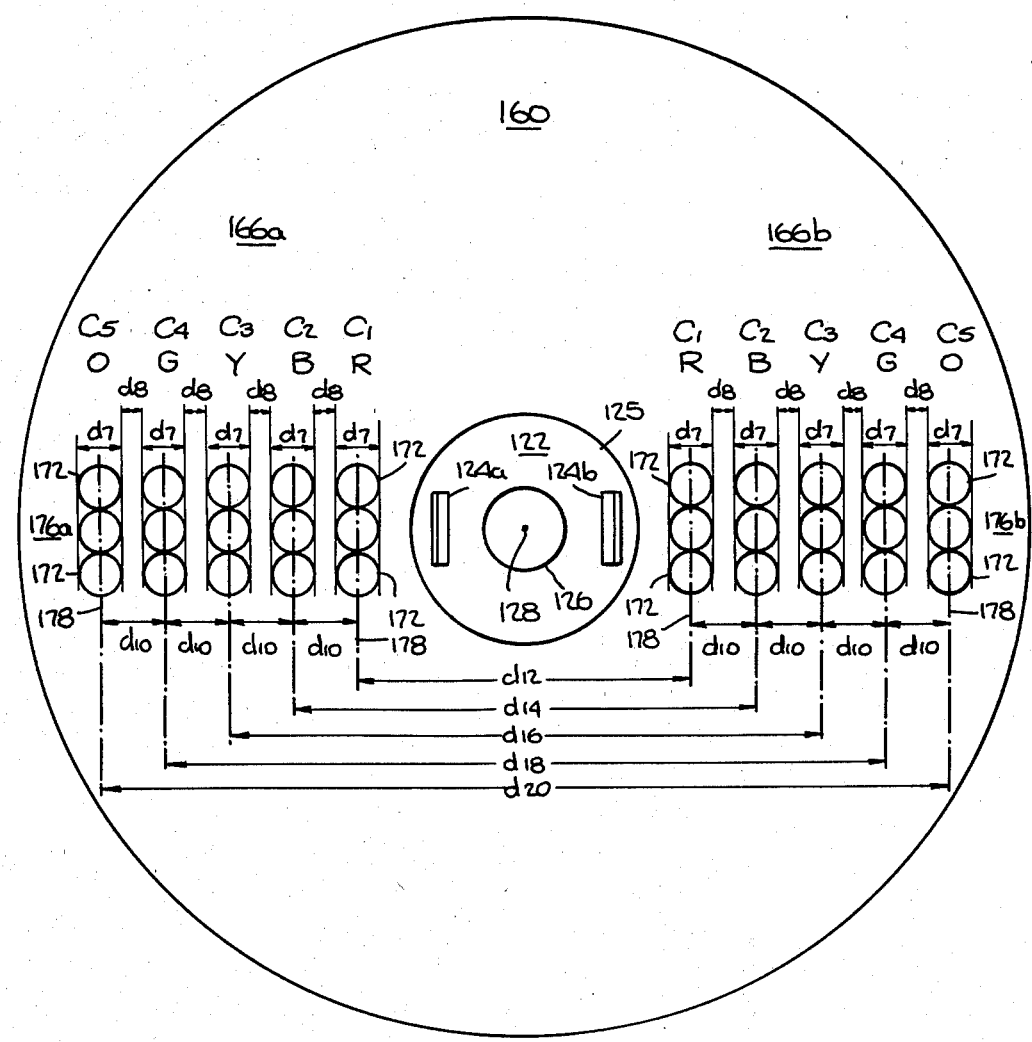
FIG. 5 is a bottom view of an optical device according to another embodiment of the present invention.
Figure 6:
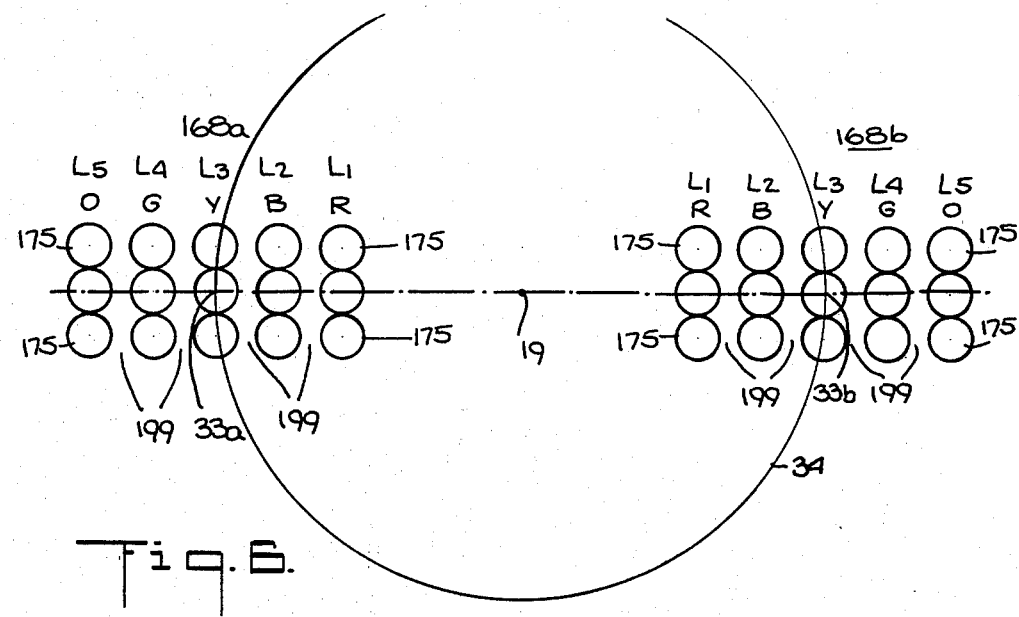
FIG. 6 is a plan view of the plane of the annular groove together with the lines of light projected from the device shown in FIG. 5.

Referring now to FIGS. 5 and 6 there is shown another embodiment of the present invention in which lines of colored light are used to determine, without any moving parts, the distance between the end points of the diameter in question. In this embodiment a goneal assembly 122 includes an annular shade or bottom flange 160 which extends laterally from and surrounds the housing 125 at the lowermost end thereof. The shape of the shade 160 preferably complements the contour of the corneal surface of the eye which is proximate thereto when the goneal assembly 122 is placed in its operable position. The shade 160 acts as a means for directing a predetermined pattern of light toward the eye, while preventing extraneous light from impinging the eye. The shade 160 includes two shade portions or flange portions 166a, 166b, located on opposite sides of the longitudinal axis 128, for directing a light pattern onto the corneal surface. The light pattern is comprised of two series 168a, 168b of lines of light L projected through the transparent corneal surface onto the plane of the annular groove 34 which is substantially perpendicular to the optic axis 19 and includes the anterior chamber diameter "D". Each series 168a, 168b is positioned at opposite sides of the optic axis 19 and spaced therefrom so that a portion of each series 168a, 168b is superpositioned on an end point 33a, 33b of the annular groove 34. The lines of light L are formed parallel to each other with each line L in a series 168a, 168b being adjacent to the other lines of the same series. A different color is imparted to each line of light L in the same series with each line of light L being properly spaced from the other lines of light L in the same series so as to be capable of illuminating an end point 33a, 33b of the annular groove 34. The illuminated end points 33a, 33b and the color of each line L illuminating an end point 33a, 33b is visible through a properly positioned goneal assembly 122. The distance from the inner and outer edges of the colored lines of light L of one series 168a to the inner and outer edges of each of the colored lines L of the other series 168b are predetermined so that the distance between the end point 33a, 33b of the annular groove 34, or in other words the anterior chamber diameter "D", can be determined from the colors of the lines of light L illuminating the end points 33a, 33b.

According to this embodiment the spacing of the lines of light L on the plane of the annular groove 34 closely corresponds to the geometric arrangement of the source of the light pattern on the shade 160. The lines of light L are projected toward the eye through like holes 172 located in the shade portions of flange portions 166a, 166b. The holes 172 are arranged into columns C, as can be seem most clearly in FIG. 5, with the holes 172 properly spaced apart within each column C so that the light pattern emanating from the holes 172 within a column C appears on the plane of the annular groove 34 as a line of light L (FIG. 6). According to one example of this embodiment the holes 172 are preferably 0.15 mm in diameter d7 and arranged into five columns C on each side of the longitudinal axis 128, ranging from innermost columns C1 to outermost columns C5. Each column C has three holes 172 and an imaginary center line 178 passing through the center of the holes 172. The width of each column corresponds to the diameter (0.15 mm) of each hole 172. The columns C on each shade portion 166a, 166b are referred to collectively as sets 176a, 176b.

The columns C within each set 176a, 176b are adjacent to one another while the columns C of both sets 176a, 176b are parallel. The perpendicular distance d8 between the periphery of each hole 172 and the nearest hole 172 of the adjacent column is preferably 0.10 mm. Each hole 172 within a column C is barely spaced apart from the nearest hole 172 in the same column C so that the light pattern appear as contiguous dots of light 175 on the plane of the annular groove 34 touching each other along the center lines 178. The center line 178 of each column C is preferably separated from the adjacent center line 178 by a distance d10 of 0.25 mm.

The bottom flange or shade 160 is constructed so that it extends beyond the end points 33a, 33b of the annular groove 34 of any human eye under examination, when the goneal assembly 122 is placed in its operable position. The anterior chamber diameter "D" of human eyes is generally between 11.5 mm and 13.5 mm with the optic axis 19 passing approximately through the midpoint of the diameter "D". The shade 160 is annular in shape, surrounds the housing 125 and preferably has an inner radius extending outward from the longitudinal axis 128 of the housing 125 of less than or equal to 5.75 mm to an outer radius equal to or in excess of 6.75 mm. The shade 160 consequently extends beyond the end points 33a, 33b of any eye under examination. In addition, the columns C are arranged on oppoite sides of the longitudinal axis 128 with the perpendicular distances d12, d14, d16, d18, d20 between the center lines 178 of the columns C1–C5 of each set 176a, 176b being fixed at 11.5 mm, 12.0 mm, 12.5 mm, 13.0 mm and 13.5 mm respectively.

According to this embodiment of the invention there is located at a distance from the shade 160 a light source with thirty optic fiber bundles maintained in a light-receiving relationship therewith (not shown). One bundle is connected to each of the thirty holes in the shade 160 so as to transmit light beams therethrough. The optic fiber bundles transfer the light received from the light source at their receiving ends through their lengths to the opposite ends where they transmit light beams in the direction that the ends are oriented.

Colors are imparted to the light beams that pass from the holes 172 of the shade 160 onto the plane of the annular groove 34 in a manner so that each column C within a set 168a, 168b emits a different color than the other columns within the same set. The colors are preferably imparted by inserting a filter or colored piece of glass in each of the holes 172. The same type of filter or glass is inserted within each hole of a column C so that the light transmitted from the ends of the optic fiber bundles in a column C produce dots of light 175 with the desired color. The dots of light 175 emanate from the holes 172 within each column C close enough to one another so as to produce a colored line of light L on the plane of the annular groove 34. The result is a series 168a, 168b of five colored lines of light L on each side of the optic axis 19 ranging from innermost lines L1 to outermost lines L5, corresponding respectively to the five columns C1–C5 on each side of the longitudinal axis 128, and with a sequence of colors from lines L1 to lines L5 of red R, blue B, yellow Y, green G and orange O. The series 168a, 168b are symmetrical and mirror images of one another about the optic axis 19 in terms of position and color. By proper spacing of the holes 172 through which the optic fiber bundles transmit beams of light, a line of light L is obtained from each column C with a distinct separation or dark band 199 between each colored line of light L. It is also possible to position the holes 172 so that the lines of light L are close enough together so as to omit the dark band 199 by forming a fringe area where two adjacent colored lines of light just touch one another (not shown).

The five colored lines of light on each side of the optic axis 19 include component dots of light 175 formed by the transmission of light beams through the holes 172. The viewer can determine by looking through the goneal assembly 122, which includes lens 127, eyepiece 126 and mirrors 124a, 124b, that, as indicated in FIG. 6, the yellow lines Y transmitted through the transparent corneal surface are responsible for illuminating the end points 33a, 33b of the annular groove 34. The distance between corresponding inner edges of the pair of yellow lines Y is 12.35 mm. The distance between corresponding outer edges of the pair of yellow lines Y is 12.65 and the center to center distance between the pair of yellow lines Y is 12.5 mm. From this pattern it can be determined, prior to surgery in the doctor's office that ocular lenses with sizes of 12.35 to 12.65 mm should be kept on hand in the operating room for surgical implantation into this eye 17. It is therefore possible, according to the geometric arrangement of the lines 170 in this embodiment, to determine the anterior chamber diameter "D" within a range of 0.30 mm.

A viewer cannot see the green lines G and orange lines O through the goneal assembly 122 since they are beyond the end points 33a, 33b and in the region of the light-impervious ciliary body (not shown) and, accordingly, not transmitted into the anterior chamber of the eye. The blue lines B located within the anterior chamber, and closer to the optic axis 19 than the yellow lines Y, are visible by the viewer through the goneal assembly 122. The colored lines of light L are spaced apart so that a determination can easily be made of the color of the lines responsible for the illumination of the end points 33a, 33b. It is also possible, to make an approximation of the anterior chamber diameter "D" within the same range where the end points are not illuminated because the dark bands 199 are superpositioned on the end points 33a, 33b.

For example, if the anterior chamber diameter "D" of the eye under examination were 12.25 mm then in accordance with the device embodied in FIGS. 5 and 6 the end point 33a, 33b would be positioned behind the dark band 199 between the blue lines B and yellow line Y of series 168a, 168b. The blue lines B of each series 168a, 168b would be visible through the goneal assembly 122, however, the end points 33a, 33b and the yellow lines Y would not be visible as they would be located beyond the anterior chamber in the region of the ciliary body. From this view it may be determined that the end points 33a, 33b are located between the blue lines B and yellow lines Y on each side of the optic axis 19 and, accordingly, a diameter "D" between 12.15 and 12.35 mm would be indicated.

It is obvious that numerous variations in the number and width of the lines of light are possible from which the anterior chamber diameter "D" can be determined within defined ranges. It is also possible to determine the anterior chamber diameter if the lines of light L are not mirror images of one another with respect to the optic axis 19, if the distances between the lines L are predetermined and the lines are distinguishable from one another in terms of color.

Furthermore, it is possible to form lines of light L on the plane of the annular groove 34 in a different manner than the aforedescribed use of optic fibers and holes 172 in the bottom flange 160, such as through the use of slits in the bottom flange or shade 160 described below with respect to lines of light in the form of concentric arcs.

Figure 7:
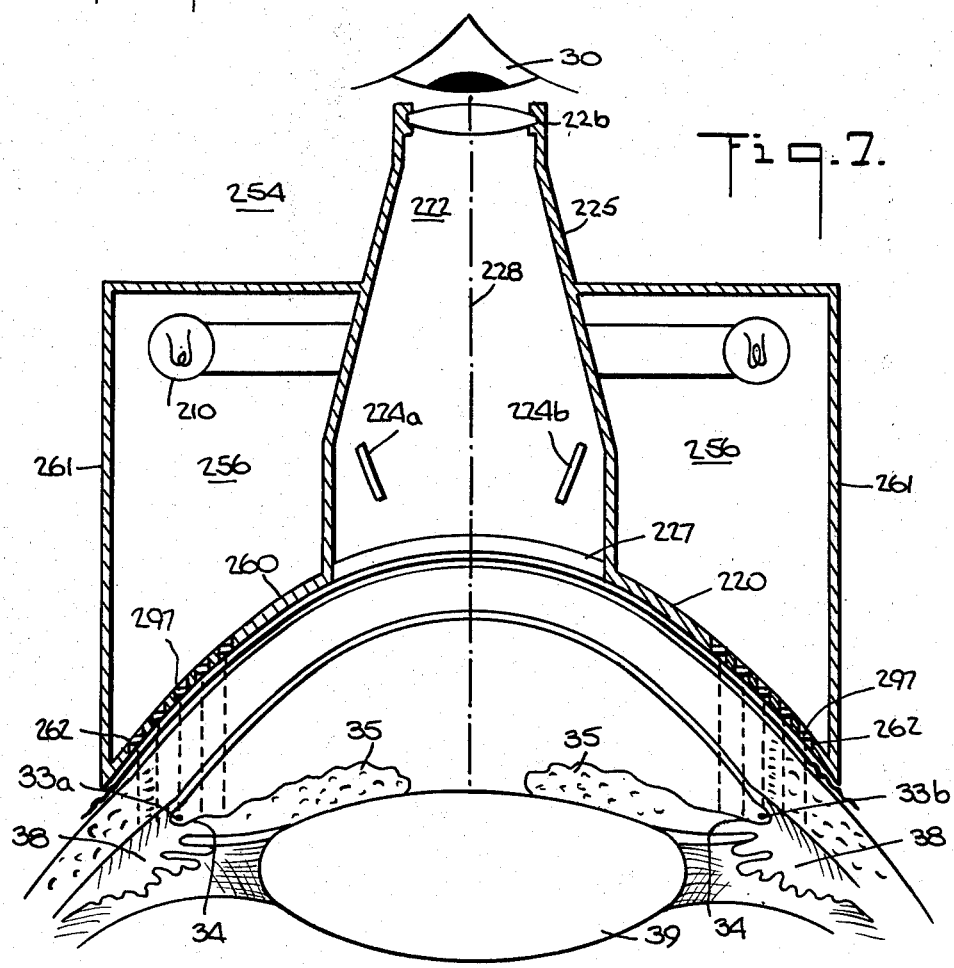
FIG. 7 is a sectional view of an optical device according to another embodiment of the present invention together with a schematic sectional view of an eye to be measured.
Figure 8:
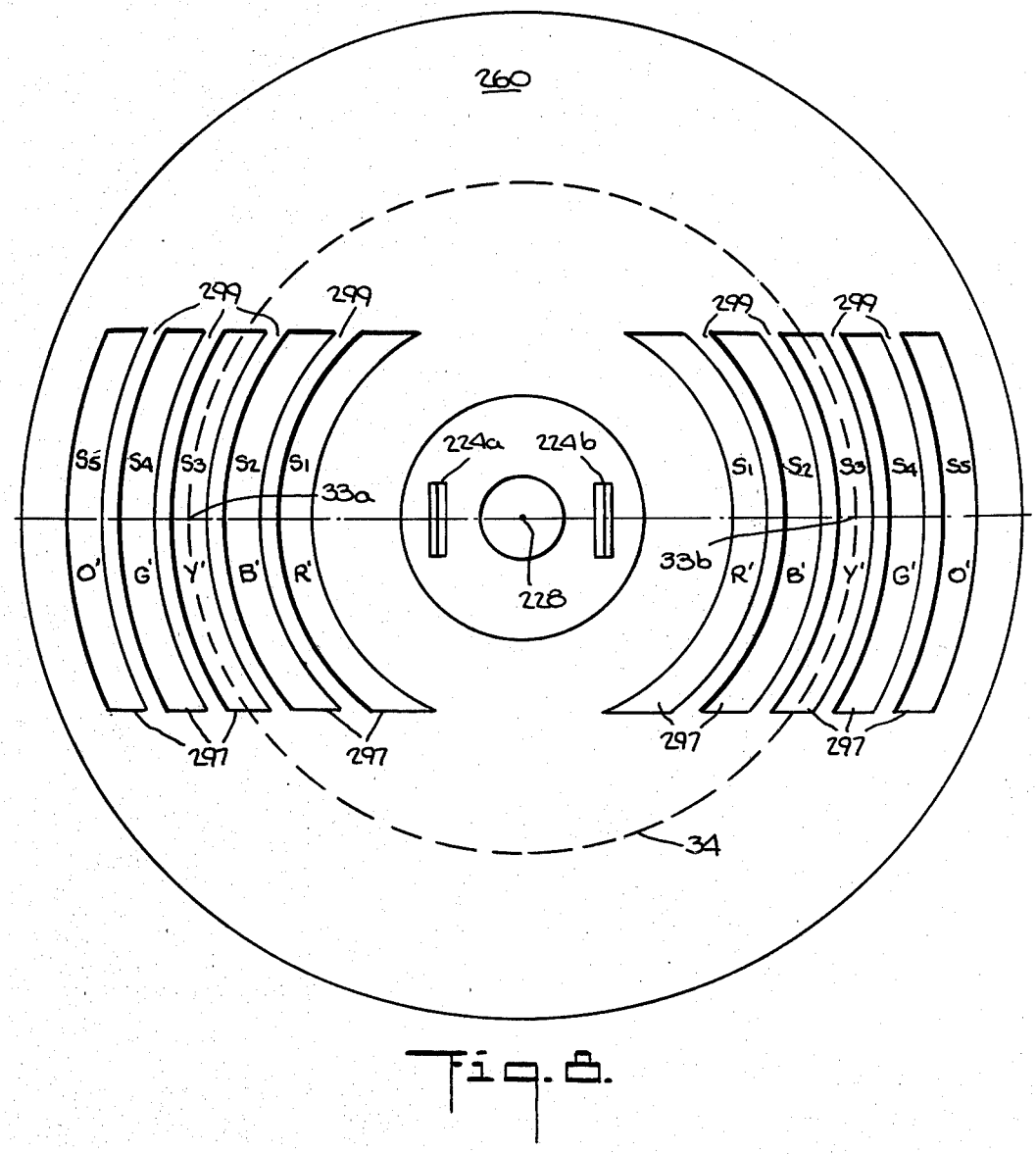
FIG. 8 is a bottom view of device shown in FIG. 7 together with the periphery of the annular groove.

Referring now to FIGS. 7 and 8 in which the goneal assembly 222 includes a housing 225, eyepiece 226, lens 227, and mirrors 224 a, b. The goneal assembly 222 is further equipped with an enclosure 254 that surrounds chamber 256 and includes a top flange 257 and bottom flange or shade 260 interconnected by sidewall 261. Located within the chamber 256 is a light source 210 that is annular in shape and surrounds the housing 225. The bottom flange 260 has a plurality of arc shaped slits S that are concentric with respect to the longitudinal axis 228 passing through the origin so that the slits S are also concentric with respect to the optic axis 19 when the goneal assembly 222 is placed in an operable position. The bottom flange or shade 260 is similar in shape and extent to that shown in FIG. 5, namely, the bottom flange 260 complements the shape of the corneal surface of the eye and extends from the longitudinal axis 228 of the housing 225 with a radius of less than or equal to 5.75 mm to a radius greater than or equal to 6.75 mm. In this manner the bottom flange 260 extends beyond the end points 33a, 33b of any eye under examination.

According to one example of this embodiment there are five arc-shaped slits S positioned on each side of the longitudinal axis 228, ranging from innermost slits S1 to outermost slits S5. The slits S are preferably 0.15 mm in width with the innermost slits S having an inner diameter of 11.35 mm and an outer diameter of 11.65 mm and a central diameter of 11.5 mm. The inner, outer and central diameters of the remaining slits S2–S5 are as follows: 11,85, 12.15, 12.0, 12.35, 12.65, 12.5, 12.85, 13.15, 13.0 and 13.35, 13,65, 13.50 respectively.

Located within each slit S is a filter or piece of glass 297 so that the light passing through each slit S acquires a different color, shown here as red R', blue B', yellow Y', green G' and orange O'. There is an optical system (not shown) associated with the light source 210 so that when the goneal assembly 222 is placed in its operable position the light passing through the slits S1–S5 produce five clear and distinct concentric arcs of light (not shown) on the plane of the annular groove 34 at each of two opposite sides of the optic axis 19. The colored concentric arcs of light have a similar geometrical arrangement with respect to the optic axis 19 that the concentric slits S1–S5 have with respect to the longitudinal axis 228. Between adjacent concentric slits are opaque bands 299 having a width of 0.10 mm which produce dark bands on the surface of the eye.

Since the annular groove 34 of the anterior chamber is substantially circular in shape the use of arc shaped lines of light lends itself to superpositioning of the arc shaped lines of light onto a portion of the annular groove 34. For example, as shown in FIG. 8, upon proper positioning of the goneal assembly 222 during examination of an eye having an anterior chamber diameter "D" of 12.50 mm the yellow arc of light Y' illuminates a portion of the periphery of the annular groove 34 at which time each of the end points 33a, 33b will be illuminated and visible through the goneal assembly 222. The annular groove 34 is shown superimposed on the bottom flange 260 as a dashed circle. To the viewer observing through goneal assembly 222 the inner blue arc of light B' will be visible while the outermost green G' and orange O' arcs are beyond the end points 33a, 33b and in the vicinity of the light-impervious ciliary body (not shown) and therefore not visible. The yellow arcs of light Y' have an inner diameter of 12.35 and an outer diameter of 12.65 mm from which it can be determined that the anterior chamber diameter "D" is within the range of 12.35 to 12.65 mm.

If the anterior chamber diameter "D" of the eye under examination were 12.25 mm, then according to the configuration shown, the end points would not be illuminated since the dark bands 299 would be superpositioned on each end point. However, since the blue arc of light B' would be visible through the goneal assembly 222, it is apparent that the diameter would be determined as within the range covered by the dark band of 12.15 to 12.35 mm.

As described previously with respect to parallel lines of light, variation in the number, color and width of the concentric circles of light are possible for determining the anterior chamber diameter within defined ranges. It is also apparent that the anterior chamber diameter "D" can be determined from colored circles of light formed by passing light through a series of properly spaced slits of concentric circles having the longitudinal axis as the origin. The diameters of each circle of light is predetermined and a different color is imparted to each circle of light. From the color of the circle of light illuminating each end point and by knowing the diameter of each circle of light illuminating each end point the anterior chamber diameter "D" can be determined.

It is to be understood that the enclosure 256 together with the light source 210 can be a separate unit that is capable of being mounted on an existing goneal assembly. Furthermore a light source other than one present in the chamber can be used to provide light beams for passage through the slits. For example an overhead light may be used wherein the top flange and sidewall are eliminated from the enclosure 256 so that the slits in the bottom flange or shade are accessible to the light beams.

It is also to be understood that the foregoing description of the preferred embodiments of the present invention is for the purposes of illustration only and that the various structural and operational features and relationships herein described are susceptible to a number of modification and change none of which entails any departure from the spirit and scope of the present invention and as defined in the hereto appended claims.

I claim:

1. In an ocular apparatus having a goneal assembly positionable proximate to the anterior surface of the cornea for viewing the presence of light, at first and second opposite end points of a diameter of the annular groove, said goneal assembly having a goneal housing and a longitudinal axis approximately coinciding with the optic axis when said assembly is in an operable position, said optic axis passing approximately through the midpoint of said diameter, said annular groove being formed by the anterior surface of the iris and the posterior surface of the cornea, the annular groove being bounded by a light-impervious ciliary body outwardly of the groove with respect to the optical axis of the eye, the improvement comprising:

light means cooperative with said goneal assembly for directing light toward the eye;

flange means including first and second flange portions extending laterally from said goneal housing so as to be anterior and proximate to the corneal surface of the eye and at first and second opposte sides of said optic axis, respectively, when said goneal assembly is in an operable position; and color means cooperating with said flange means for transmitting light beams onto the surface of the eye in the form of a first and second series of lines of light at opposite sides of the optic axis, each line of light being of a different color than and adjacent to other lines of light in the same series, said lines of light being spaced at predetermined distances from one another and adapted to illuminate said first and second end points with first and second colored lines of light from said first and second series, respectively, when the light is directed through said color means in regions corresponding to the annular groove and in regions corresponding to said light-impervious ciliary body, the colors of said first and second lines illuminating said first and second end points being visible through said goneal assembly whereby said anterior chamber diameter is determinable from the color of said first and second colored lines and corresponds to the predetermined distance therebetween.

2. In an ocular apparatus as claimed in claim 17, the anterior chamber diameter of human eyes having a dimensional range with a predetermined maximum and minimum dimension, wherein said first series is a mirror image of said second series with respect to said optic axis, each series having an innermost line and an outermost line with respect to said optic axis, the perpendicular distance measured along a diameter passing through said optic axis between said innermost line of said first and second series being less than or equal to said minimum dimension, the perpendicular distance measured along a diameter passing through said optic axis between said outermost line of said first and second series being greater than or equal to said upper dimension.

3. In an ocular apparatus as claimed in claim 2 wherein said first and second series have an identical sequence of line colors from innermost line to outermost line.

4. In an occular apparatus as claimed in claim 1 wherein the surfaces of said first and second flange portions are complementary to the respective surfaces of the eye proximate thereto.

5. In an ocular apparatus as claimed in claim 20 wherein each line of light is in the shape of an arc of a circle, said circle having a common origin, approximately coinciding with the optic axis.

6. In an ocular apparatus as claimed in claim 5 wherein said first and second series are mirror images of one another with respect to said optic axis.

7. In an ocular apparatus as claimed in claim 1 wherein said lines of light are parallel to one another.

8. In an ocular apparatus as claimed in claim 1 wherein said color means includes a first and second sequence of parallel slits extending through said first and second flange portions, respectively, each slit being properly positioned so as to form a corresponding line of light in said first and second series of lines of light on the surface of the eye when light beams are transmitted from a light source therethrough.

9. In an ocular apparatus as claimed in claim 8, wherein said coloring means includes a filter occupying each of said slits for imparting color to said light beams passing through said slits.

10. An ocular apparatus as claimed in claim 1 wherein said color means includes a plurality of like holes in said first and second flange portions, a plurality of optic fiber bundles, each bundle having two ends, a receiving end positionable proximate to a light source and in light receiving relationship therewith and a transmitting end extending toward said flange portions for transmitting light as light beams and connecting means for connecting each of said bundles to a corresponding hole in said flange portions so that said optic fiber bundles transmit said light beams through said holes onto the corneal surface of the eye, said light beams transmitted through said holes forming said first and second series of colored lines on said corneal surface of the eye when said goneal assembly is in an operable position.

11. An ocular apparatus as claimed in claim 10 wherein said coloring means includes means within each hole for imparting color to the light beams transmitted from the transmitting end of said optic fiber bundle.

12. An ocular apparatus as claimed in claim 10 wherein said coloring means includes a means for imparting a color to the light received by said receiving end of said optic fiber bundles.

13. In an ocular apparatus having a goneal means positionable proximate to the anterior surface of the cornea for viewing the presence of light at first and second opposite end points of a diameter of the annular groove formed by the anterior surface of the iris and the posterior surface of the cornea and bounded by a light-impervious ciliary body outwardly of the groove with respect to the optic axis of the eye, said goneal means having a longitudinal axis approximately coinciding with said optic axis when said goneal means is in an operable position, said optic axis passing approximately through the midpoint of said diameter, the improvement comprising:

light means for directing light toward the eye; and
means cooperating with said light means for transmitting light beams onto the surface of the eye in the form of a first and second series of lines of light at opposite sides of said optic axis, each line of light being adjacent to other lines of light in the same series, said lines of light being spaced at predetermined distances from one another and adapted to illuminate said first and second end points with first and second lines of light from said first and second series, respectively, when the light is directed through said means to regions corresponding to the annular groove and to regions corresponding to said light-impervious ciliary body, said first and second lines illuminating said first and second end points being visible through said goneal means whereby said anterior chamber diameter is determinable from the positions of said first and second lines and corresponds to the predetermined distance therebetween.

14. In an ocular apparatus having a goneal assembly positionable proximate to the anterior surface of the cornea for viewing the presence of light at first and second opposite end points of a diameter of the annular groove formed by the anterior surface of the iris and the posterior surface of the cornea and bounded by a light-impervious ciliary body outwardly of the groove with respect to the optic axis of the eye, said goneal assembly having a longitudinal axis approximately coinciding with said optic axis when said assembly is in an operable position, said optic axis passing approximately through the midpoint of said diameter, the improvement comprising:

light means cooperative with said goneal assembly for directing light toward the eye; and
color means cooperating with said light means for transmitting light beams onto the surface of the eye in the form of a first and second series of lines of light at opposite sides of said optic axis, each line of light being of a different color than and adjacent to other lines of light in the same series, said lines of light being spaced at predetermined distances from one another and adapted to illuminate said first and second end points with first and second colored lines of light from said first and second series, respectively, when the light is directed through said color means to regions corresponding to the annular groove and to regions corresponding to said light-impervious ciliary body, the colors of said first and second lines illuminating said first and second end points being visible through said goneal assembly whereby said anterior chamber diameter is determinable from the color of said first and second colored lines and corresponds to the predetermined distance therebetween.

* * * * *